US012685470B2

(12) United States Patent
Perrot et al.

(10) Patent No.: US 12,685,470 B2
(45) Date of Patent: Jul. 21, 2026

(54) DEVICE AND A COMPUTER-IMPLEMENTED METHOD FOR DETERMINING A BEHAVIOR OF A TARGET USER

(71) Applicant: Essilor International, Charenton-le-Pont (FR)

(72) Inventors: Stephane Perrot, Charenton-le-Pont (FR); Matthias Guillon, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 524 days.

(21) Appl. No.: 18/245,669

(22) PCT Filed: Sep. 15, 2021

(86) PCT No.: PCT/EP2021/075278
§ 371 (c)(1),
(2) Date: Mar. 16, 2023

(87) PCT Pub. No.: WO2022/058326
PCT Pub. Date: Mar. 24, 2022

(65) Prior Publication Data
US 2023/0355149 A1 Nov. 9, 2023

(30) Foreign Application Priority Data

Sep. 17, 2020 (EP) .................................... 20306042

(51) Int. Cl.
*A61B 3/14* (2006.01)
*A61B 3/00* (2006.01)
(Continued)

(52) U.S. Cl.
CPC ............ *A61B 5/163* (2017.08); *A61B 3/0008* (2013.01); *A61B 3/0025* (2013.01); *A61B 3/06* (2013.01);
(Continued)

(58) Field of Classification Search
CPC ....... A61B 3/0008; A61B 3/0025; A61B 3/06; A61B 3/113; A61B 3/14; A61B 5/163;
(Continued)

(56) References Cited

U.S. PATENT DOCUMENTS 9,600,069 B2 3/2017 Publicover et al.
11,733,542 B2 * 8/2023 Macnamara ............ G06T 13/40
351/206
(Continued)

FOREIGN PATENT DOCUMENTS

CN 106663183 A 5/2017
KR 10-2016-0098235 A 8/2016
(Continued)

OTHER PUBLICATIONS

International Search Report mailed on Dec. 8, 2021 in PCT/EP2021/075278 filed on Sep. 15, 2021, 4 pages).
(Continued)

*Primary Examiner* — Mahidere S Sahle
(74) *Attorney, Agent, or Firm* — Oblon, McClelland, Maier & Neustadt, L.L.P.

(57) ABSTRACT

A device for determining a behavior of a target user, the device including a sensing unit configured to face at least one eye area of a target user, the sensing unit being configured to acquire a plurality of target signals representative of a variation of at least one characteristic of the at least one eye area of the target user, the sensing unit including at least one sensor, and the at least one sensor being oriented towards the eye area. The device also includes a controller configured to
(Continued)

provide a machine learning algorithm, provide a plurality of objective target data related to the acquired target signals as an input to the machine learning algorithm, and determine a behavior of the target user as an output of the machine learning algorithm.

12 Claims, 4 Drawing Sheets

(51) Int. Cl.

| | |
|---|---|
| *A61B 3/06* | (2006.01) |
| *A61B 3/113* | (2006.01) |
| *A61B 5/00* | (2006.01) |
| *A61B 5/11* | (2006.01) |
| *A61B 5/16* | (2006.01) |
| *G06N 20/00* | (2019.01) |

(52) U.S. Cl.
CPC .............. *A61B 3/113* (2013.01); *A61B 3/14* (2013.01); *A61B 5/1103* (2013.01); *A61B 5/7267* (2013.01); *G06N 20/00* (2019.01); *A61B 5/1128* (2013.01)

(58) Field of Classification Search
CPC ... A61B 5/1103; A61B 5/7267; A61B 5/1128; G06N 20/00
USPC .......................................... 351/206, 208–210
See application file for complete search history.

(56) References Cited

U.S. PATENT DOCUMENTS

| | | | |
|---|---|---|---|
| 2016/0157712 | A1 | 6/2016 | Borden et al. |
| 2017/0100032 | A1 | 4/2017 | Zakariaie et al. |
| 2018/0161579 | A1 | 6/2018 | Franke et al. |
| 2019/0205607 | A1 | 7/2019 | Hong |
| 2019/0258930 | A1 | 8/2019 | Ohlendorf et al. |
| 2020/0129063 | A1 | 4/2020 | McGrath et al. |
| 2020/0170560 | A1 | 6/2020 | Zakariaie et al. |
| 2020/0214559 | A1 | 7/2020 | Krueger et al. |
| 2020/0363867 | A1 | 11/2020 | Azimi et al. |

FOREIGN PATENT DOCUMENTS

| | | | |
|---|---|---|---|
| KR | 10-2019-0005847 | A | 1/2019 |
| KR | 10-2020-0017576 | | 2/2020 |
| WO | WO 2016/203212 | A2 | 12/2016 |
| WO | WO-2017/116662 | A1 | 7/2017 |
| WO | WO 2019/152619 | A1 | 8/2019 |

OTHER PUBLICATIONS

European Search Report dated Mar. 4, 2021 in EP Application 20306042.1 filed on Sep. 17, 2020, 12 pages).

Korean Office Action issued Nov. 30, 2024 in Korean Patent Application No. 10-2023-7003959, (with English translation), 16 pages.

Combined Chinese Office Action and Search Report issued Sep. 20, 2025 in Chinese Patent Application No. 202180063746.5, (with English translation), 18 pages.

Combined Chinese Office Action and Search Report issued Mar. 24, 2025 in Chinese Patent Application No. 202180063746.5 (with English translation), therein, 20 pages.

European Office Action issued Nov. 13, 2025 in European Patent Application No. 21773826.9, 9 pages.

Canadian Office Action issued Jul. 25, 2025 in Canadian Patent Application No. 3,186,540, 7 pages.

* cited by examiner

DISCOMFORT

| | | |
|---|---|---|
| 8 | — | Unbearable |
| 7 | — | Really disturbing |
| 6 | — | Disturbing |
| 5 | — | Just disturbing |
| 4 | — | Perceptible |
| 3 | — | Just Perceptible |
| 2 | — | Negligible discomfort |
| 1 | — | Almost not noticeable |
| 0 | — | No discomfort |

DEVICE AND A COMPUTER-IMPLEMENTED METHOD FOR DETERMINING A BEHAVIOR OF A TARGET USER

FIELD OF THE INVENTION

The invention relates to the field of determining a behavior of a user, notably by considering at least one eye area of said user. Particularly, the invention is directed to a device for determining a behavior of a target user. The invention further concerns a computer-implemented method for determining a behavior of a target user.

BACKGROUND OF THE INVENTION

An eye area is notably composed of the eye, the eyelid and muscles surrounding the eye. Depending on the conditions encountered by the user or actions the user wants to perform, the user may have a behavior inducing a change of one or more of these components of the eye area. This behavior may be a change in the visual comfort, as glare, a movement of the eye or a change in the dimension of the pupil or eyelid movement or muscle strains. The behavior of the user is usually a response to an external stimulus (e.g. light stimulation), a voluntary action performed by the user (e.g. focusing his vision on an object) or a psychological reaction of the user (e.g. an emotion experienced by the user). Determining a link between a change of the eye area and a behavior of the user is very complex because the eye area comprises many muscles and can have various states.

It is known in the art to use sensors to measure specific physiological characteristics of the eye area of a user to correlate a variation of this specific physiological characteristics with a behavior. An example of such a method is provided in EP19306731. This known method implies that the component or the portion of the eye area which is measured by the sensors is previously determined and that the behavior is determined depending on that specific measurements. This method requires to first determine a correlation between a variation of a physiological characteristic of the eye area and a behavior of the user. As an example, a correlation must be first determined between an eye closure or a variation of the position of the eyelid and glare. However, it is highly difficult to correlate a variation in the activity of a specific muscle around the eye and a behavior of the user. It is therefore even more difficult to correlate various variations encountered by the eye area with a behavior of the user. Furthermore, a same variation of the eye area for two different users cannot necessarily be interpreted as a same behavior for the users. Indeed, glare may imply eye closure for a user and only a variation in the activity of the muscles around the eye for another user. Therefore, even a basic behavior may be difficult to correlate to a physical variation of the eye area.

A fortiori, complex behaviors involving limited variations or complex combined variations of the eye area may thus be even more difficult to determine using analytical determination.

Furthermore, determining complex behaviors which induce many variations of the eye area may imply the use of many sensors and a strong calculation system. However, even with a strong calculation system, it is too difficult to accurately determine complex behaviors of the user using this analytical method.

There is therefore a need for a device able to correlate a change in an eye area of a user with a behavior of this user in a more accurate manner

SUMMARY OF THE INVENTION

To that end, the invention provides a device for determining a behavior of a target user, comprising:
- a sensing unit configured to face at least one eye area of a target user, the sensing unit being configured to acquire a plurality of target signals representative of a variation of at least one characteristic of said at least one eye area of said target user,
  - the sensing unit comprising at least one sensor, and
  - the at least one sensor being oriented towards the eye area; and
- a controller configured to:
  - provide a machine learning algorithm,
  - provide a plurality of objective target data related to the acquired target signals as an input to said machine learning algorithm,
  - determine a behavior of said target user as an output of the machine learning algorithm.

Said device uses a machine learning algorithm to correlate objective target data related to the acquired target signals to a behavior. A machine learning algorithm is able to process very complex signals and then correlate said complex signals to certain behaviors. We can thus obtain an objective determination of a behavior.

In doing so, a behavior is determined without any assumptions about the state in which the eye area is supposed to be. It allows to avoid using very precise and fastidious analytic signal processing of such variations of characteristics, e.g. subtle and various variations of muscles around the eye. Particularly, it may avoid the use of subjective target data coming from the target user to determine the behavior, which is an important benefit with regard to the known methods. In other words, the determination of the behavior may be automatically performed, i.e. without any action or data from the target user after the method is launched.

Furthermore, the acquired target signals are more exhaustively exploited because some data are too complex, or too numerous to be detected using classical analytic methods.

The at least one sensor may be a non-imaging sensor.

Another advantage is that such behavior determination using machine learning algorithm, does not require complex signals, as images and videos, to determine the behavior of the target user. These complex signals require important power supply, provide large flow of data which require large calculation capacities. It is therefore possible to determine complex behavior with basic signals acquired with the sensing unit. The sensor of the sensing unit may be a simple pixel, such as a non-imaging sensor, a radiometer, an unique photodiode. Therefore it is possible to obtain imaging systems or complex signals systems with non imaging sensors. The use of basic signals allows these drawbacks to be avoided.

Non imaging sensors refer to a type of sensor which provides a single pixel as output. This type of sensors includes, but is not restricted to, a radiometer and a photodiode.

Furthermore, using a non-imaging sensor allows us to build very light systems in terms of power supply and with a very small hardware.

A non-imaging sensor may be opposed to an imaging sensor which provides an output comprising a plurality of pixels forming an image or a plurality of images, as a video.

The at least one sensor of the at least one sensor may be sensitive to infrared light, visible light, UV light. In other words, the sensor may acquire a signal from infrared light, visible light, UV light. The use of sensor sensitive to infrared presents the advantage not to disturb the target user and to increase the ratio between signal and noise. Each sensor may be sensitive to the same range of light, such as infrared light. Alternatively, each sensor may be sensitive to different ranges of light, such as one in the visible light and another one in the infrared light.

This device may be configured to be worn by a user. Particularly, this device is preferably configured to be positioned and supported onto the head of the user to be able to face at least one eye area of the target user.

Said device may be used to determine a parameter representative of eye strain.

Said device may be used to determine the electrochromic lenses, in particular the transmission of the electrochromic lenses.

Said device may be used into a phoropter or to determine electrochromic lenses.

According to an embodiment of the device, which can be considered alone or in combination, the sensing unit comprises at least two non-imaging sensors.

According to an embodiment of the device, which can be considered alone or in combination, the at least one non-imaging sensor is associated to at least one light source.

According to an embodiment of the device, which can be considered alone or in combination, the sensing unit comprises at least one light source.

By "associated", we mean that the sensor and the light source are synchronized in frequency/temporally and/or that the light source is oriented towards the eye area.

This embodiment presents the advantage to reduce the ratio signal under noise.

Said at least one light source is configured to emit a light signal towards at least one eye of the user. In other words, said light source acts as a transmitter of a light signal. The light signal is reflected by the eye area and then received by said at least two sensors to be processed. The sensors therefore act as receivers of a light signal. The device may comprise a light source associated to a plurality of sensors. Alternatively, a light source may be associated to only one sensor to form a pair transmitter/receiver. In this latter case, a light source and a sensor may be provided together within a same housing to form a sensing cell configured for transmission and reception of light signals.

Comparison between the transmitted light signal and the received light signal allows the controller to determine a variation of said at least one signal. In doing so, it is possible to determine a variation of a physical characteristic of the eye area. For example, when the light signal is emitted towards an eyelid and the latter moves, the light signal may be no longer reflected by the skin of the eyelid but by the eye. The reflection of the light signal is different depending on the surface which reflects the light signal. It is therefore possible to determine when the position of the eyelid has changed.

Said at least one light source may be configured to emit visible light, infrared or UV light. Preferably the at least one light source is configured to emit a nonvisible light signal, e.g. an infrared light signal.

Said at least one light source and said at least one sensor are preferably configured to remotely emit and receive a light signal, respectively. In other words, the sensing unit may be configured to remotely acquire a plurality of target signals representative of a variation of at least one characteristic of said at least one eye area of said target user.

According to an embodiment of the device, the at least one light source is oriented towards the eye area.

According to an embodiment of the device, the at least one light source may be placed around the eye area in order to avoid to disturb the target user.

The sensing unit is intended to be positioned in front of the eye area of the target user with the sensors and the light source oriented towards the eye area. The sensors and the light source are positioned in front of the eye area and around the eye area. In other words, the sensors and/or the light source may be positioned away from the face of the target user, above and/or below the eye area.

According to an embodiment of the device, it further comprises at least one light stimuli source for stimulating at least one eye.

According to an embodiment of the device, the light stimuli source may be the light source.

The invention also provides a computer-implemented method for determining a behavior of a target user, the method comprising the following steps:

providing a machine learning algorithm,
    acquiring a plurality of target signals representative of a variation of at least one characteristic of at least one eye area of a target user,
    providing a plurality of objective target data related to the acquired target signals as an input to said machine learning algorithm,
    determining a behavior of said target user as an output of the machine learning algorithm.

The computer-implemented method allows to benefit from the same advantages and technical effects as those described above for the device.

According to an embodiment of the method, said machine learning algorithm is based on a plurality of initial data related to a set of initial users, said initial data comprising a plurality of acquired learning signals representative of a variation of at least one characteristic of at least one eye area for each initial user of the set.

According to an embodiment of the method, said plurality of initial data related to a set of initial users comprises subjective and objective data, said subjective data comprising the perception of the initial users of the set to a behavior caused by said variation of at least one characteristic of at least one eye area for each initial user of the set.

According to an embodiment of the method, it further comprises:

providing to the machine learning algorithm said plurality of initial data related to a set of initial users,
    training said machine learning algorithm with regard to said plurality of initial data.

According to an embodiment of the method, it further comprises:

determining subjective data related to said target user, said subjective data comprising the perception of the target user to said behavior,
    providing said subjective data related to said target user as an input of said machine learning algorithm.

According to an embodiment of the method, said behavior is a change in the visual comfort of the target user, said variation of said at least one characteristic being caused by a light stimulus provided to said at least one eye area.

According to an embodiment of the method, said change in the visual comfort of the user is glare.

According to an embodiment of the method, further comprises determining a plurality of glare classes to classify initial users with respect to light sensitivity, said step of determining a behavior comprising determining a glare class among the plurality of glare classes corresponding to the behavior of said target user.

According to an embodiment of the method, said behavior is a movement of at least one eye of the target user or a dimension of at least one pupil of the target user or muscles strains around the eyes or movement of the eyelid.

According to an embodiment of the method, said at least one characteristic comprising at least one among a position of at least one eyelid, a position of the pupil, a size of the pupil and a muscle contraction in said at least one eye area.

According to an embodiment of the method, further comprises determining at least one filter for a transparent support able to improve or to maintain the visual comfort and/or visual performance of said target user based on said behavior.

According to an embodiment, said determining method is a computer-implemented method.

BRIEF DESCRIPTION OF THE DRAWINGS

For a more complete understanding of the description provided herein and the advantages thereof, reference is now made to the brief descriptions below, taken in connection with the accompanying drawings and detailed description, wherein like reference numerals represent like parts.

DETAILED DESCRIPTION OF EMBODIMENTS

Figure 1:
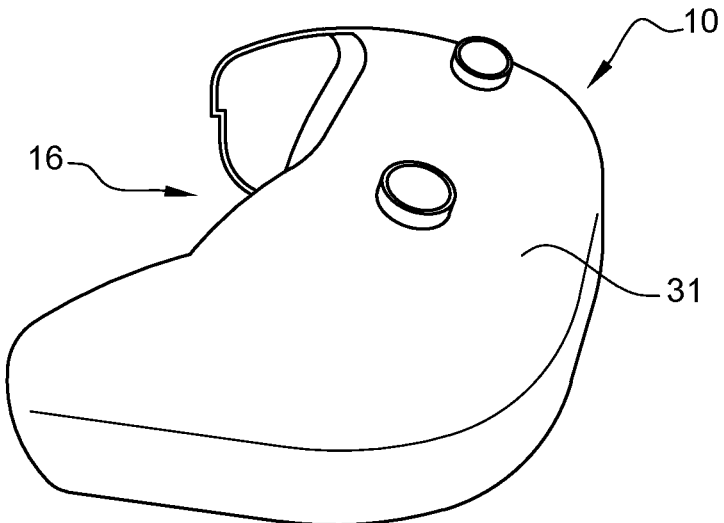
FIG. 1 schematically shows a perspective view of one side of a binocular optoelectronic device.

In the description which follows, the drawing figures are not necessarily to scale and certain features may be shown in generalized or schematic form in the interest of clarity and conciseness or for informational purposes. In addition, although making and using various embodiments are discussed in detail below, it should be appreciated that as described herein are provided many inventive concepts that may embodied in a wide variety of contexts. Embodiments discussed herein are merely representative and do not limit the scope of the invention. It will also be obvious to one skilled in the art that all the technical features that are defined relative to a process can be transposed, individually or in combination, to a device and conversely, all the technical features relative to a device can be transposed, individually or in combination, to a process.

The terms "comprise" (and any grammatical variation thereof, such as "comprises" and "comprising"), "have"

(and any grammatical variation thereof, such as "has" and "having"), "contain" (and any grammatical variation thereof, such as "contains" and "containing"), and "include" (and any grammatical variation thereof such as "includes" and "including") are open-ended linking verbs. They are used to specify the presence of stated features, integers, steps or components or groups thereof, but do not preclude the presence or addition of one or more other features, integers, steps or components or groups thereof. As a result, a method, or a step in a method, that "comprises", "has", "contains", or "includes" one or more steps or elements possesses those one or more steps or elements but is not limited to possessing only those one or more steps or elements.

The present invention provides a device for determining a behavior of a user. This device may be an eyewear device, for example a head mounted display.

The device may be a binocular device so that it is configured to face each eye area of the user in use. Alternatively, the device may be monocular and configured to face only one eye area of the user.

The device may be configured to be worn by a user. Preferably, the device is configured to be positioned and supported onto the head of the user to be able to face at least one eye area of the user. In other words, dimensions and weight of the device are configured to make it possible for a user to handle it in front of its eyes using supporting means. Said supporting means may be its hands so that the user handles the device as binoculars. Alternatively, supporting means may be means for fastening the device to the user's head as straps able to surround the user's head or spectacle arms positioned onto the user's ears. Alternatively, supporting means may be a support leg configured to sit on a table or on the ground. Furthermore, the device may comprise an accumulator to be self-sufficient in energy.

By "behavior" of the user, what is meant is a physical or physiological or psychological sensation experienced by the user. This behavior induces variations of physical characteristics of the user, especially physical characteristics of the eye area. For example, when the user experience glare, muscle activity of the eye area may occur as well as a change in the dimension of the pupil. The device is configured to determine a behavior of the user depending on these physical variations of the characteristics of the eye area.

An eye area comprises at least one among lower and upper eyelids, an eyebrow, an eyelash, an eye, the skin around the eye as well as muscle around the eye.

This behavior may be a change in the visual comfort, as glare, a movement of the eye or a change in the dimension the pupil.

By "change in the visual comfort" of the user, what is meant is an alteration of the visual comfort experienced by the user, in the form of a visual discomfort or a modification of the visual performance.

The visual comfort can be associated to the light sensitivity of the user. The device may be thus configured to determine a light sensitivity threshold of the user by monitoring the response of the user's eye areas when subjected to a given light environment.

By "sensitivity to light" of the user, what is meant is any relatively intense and prolonged reaction or modification of comfort or visual performance in relation to a temporary or continuous light flux or stimuli. The quantity representative of the sensitivity of the eye of the user to said characteristic light flux is the light sensitivity threshold. It can be determined by measuring physical responses experienced by the user or any action of the user representative of its discomfort or visual perception. It allows the visual performance and/or visual discomfort experienced by the user to be determined objectively.

Determining movements of the eye allows to track the position of the eye which can be useful in various fields, e.g. cognitive science experiments.

Said device comprises a sensing unit configured to face at least one eye area of a user. In other words, the sensing unit is intended to be disposed in front of a user face The sensing unit is also configured to acquire a plurality of target signals representative of a variation of at least one characteristic of said at least one eye area of said user. Said characteristic may comprise at least one among a position of at least one eyelid, a position of the pupil, a size of the pupil and a muscle contraction in said at least one eye area.

The sensing unit is configured to acquire said plurality of target signals representative of a variation of at least one characteristic of said at least one eye area of said user, without contact with the user. By a "without contact with the user" acquisition, we meant that the signal is acquired without positioning an electrode or a measurement element onto the eye area or the skin of the user. In other words, the acquisition of the signal is contactless between the eye area and the sensing unit. Particularly, the acquisition of said at least one signal may be performed at a distance greater than or equal to 1 cm. In a preferred embodiment, only a casing housing the sensing unit contacts the user for positioning and supporting the device onto the user's head.

The sensor of the sensing unit may be a simple pixel or a plurality of pixel, preferably one pixel. Indeed, the use of a machine learning algorithm makes it possible to significantly simplify the device by allowing the use of a simple detector, such as a pixel.

The at least one sensor may be sensitive to infrared light, visible light, UV light. In other words, the sensor may acquire a signal from infrared light, visible light, UV light. The use of sensor sensitive to infrared presents the advantage to avoid to disturb the user. Furthermore, nonvisible light is usually used to stimulate the eye during the determination process without disturb the target user and to increase the ratio between signal and noise.

Each sensor may be sensitive to the same range of light, such as infrared light. Alternatively, each sensor may be sensitive to different ranges of light, such as one in the visible light and an other one in the infrared light.

For the sake of clarity, the device is now described with reference to an embodiment of this device shown on FIGS. 1 to 4. Each feature described in conjunction with this embodiment of FIGS. 1 to 4 may be independently considered as a potential feature of the invention.

The device 10 may comprise a casing 31 forming the external envelope of the device 10. The casing 31 forms a cavity 16 intended to be positioned in front of the user's face. Preferably, a side of the casing 31 forming the cavity 16 may further comprise a profile configured to cooperate with the face of the user to position the sensing unit in front of the user's eyes. This profile may be for example configured to contact the nose and/or the forehead of the user.

Figure 2:
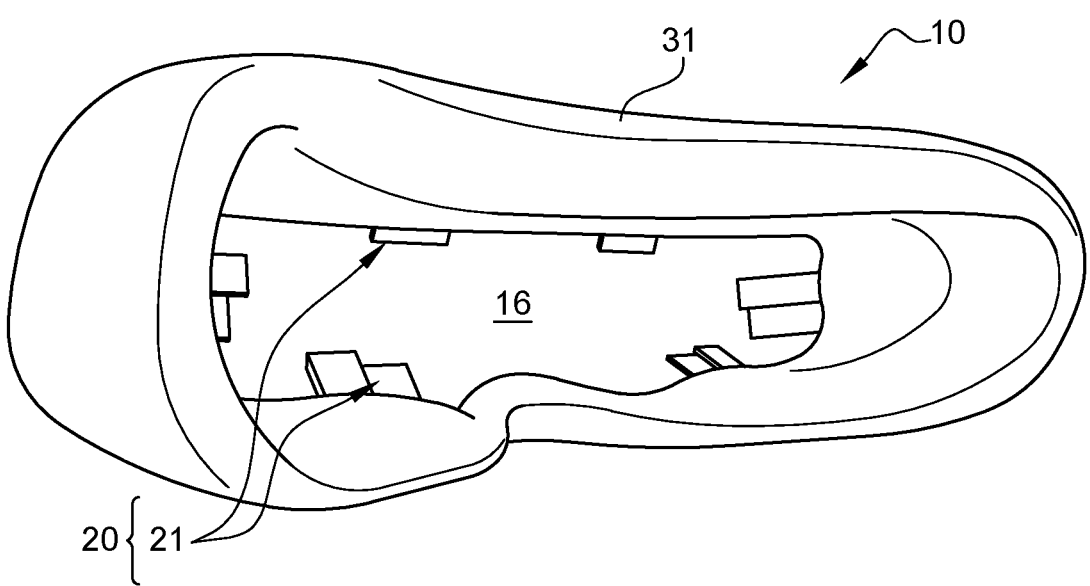
FIG. 2 schematically shows a perspective view of another side of the binocular optoelectronic device of FIG. 1.
Figure 3:
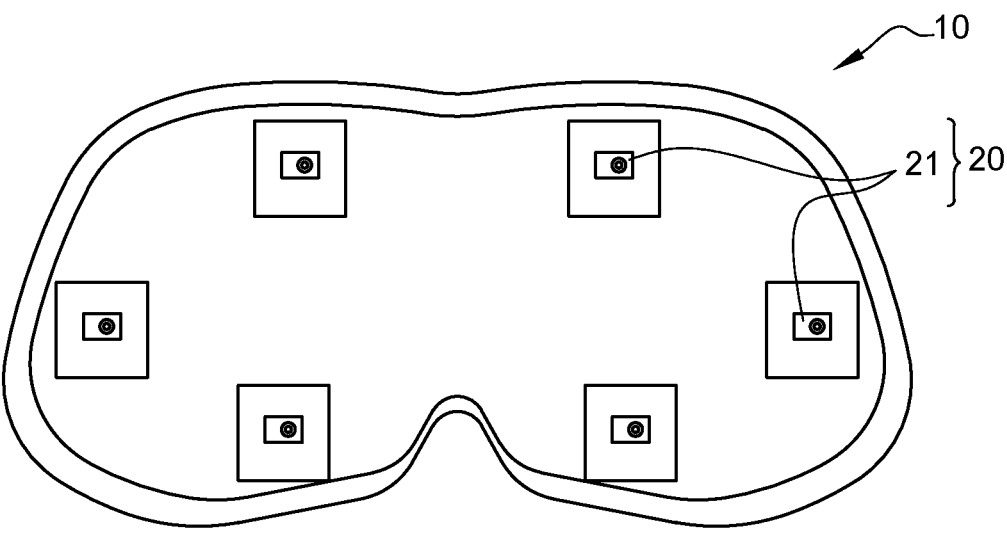
FIG. 3 schematically shows a front view of the binocular optoelectronic device of FIG. 1.

As shown on FIGS. 2 and 3, the device 10 also may comprise a sensing unit 20 having a plurality of sensing cells 21.

Each sensing cell 21 comprises a sensor to receive a light signal.

Alternatively, each sensing cell 21 comprises a sensor to receive a light signal and a light source to emit a light signal and a sensor to receive a light signal.

Each sensing cell 21 is oriented towards the user's eyes. To do so, the casing 31 of the device 10 is configured to position the eyes of the user at a predetermined position. The sensing cells 21 are positioned with regard to this predetermined position to face the eye area of the user.

As illustrated in FIGS. 2 and 3, for example, the device 10 may comprise two sensing units, each sensing unit comprising three sensing cells 21 for each eye of the user. That allows to determine the behavior of the target user for each eye of the user.

Alternatively, for example, the device 10 may comprise one sensing unit, the sensing unit comprising six sensing cells 21. That allows to determine the behavior of the target user but not specifically for one eye. It has the advantage to simplify the work of the controller.

The sensing cells 21 are preferably positioned around the eyes with different point of views and different angles to provide complementary and redundant data. It helps determining a behavior of the user to find correlation between acquired signals and behavior of the user. Having a plurality of sensing cells 21 instead of one gives the device 10 more chances to be relevant on various morphologies of user.

Figure 4:
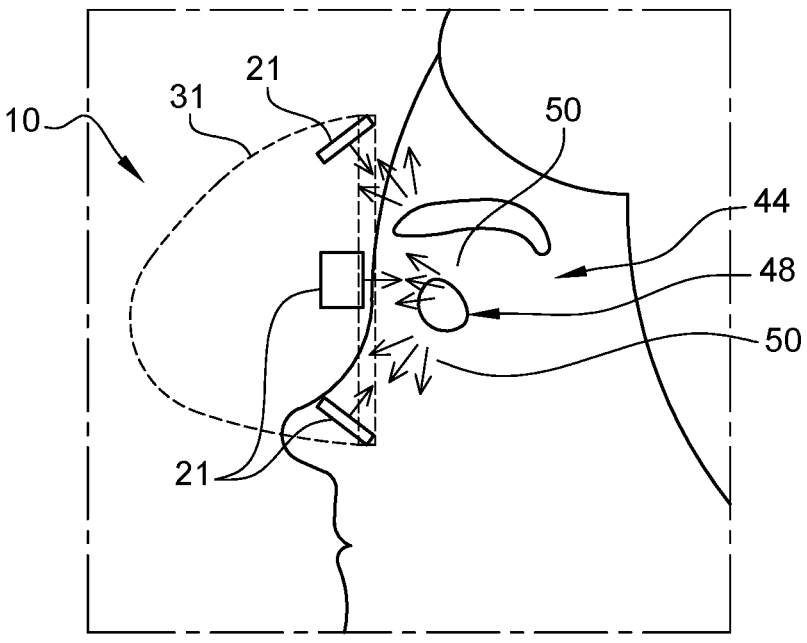
FIG. 4 schematically shows a side view of the binocular optoelectronic device of FIG. 1 worn by a user.

As shown on FIG. 4, the sensing unit 20 is intended to be positioned in front of the eye area of the target user with the sensors and the light source oriented towards the eye area. Each sensing cell 21 may be oriented towards the eyelid, the eye or a specific portion of the eye area. The sensors may be also oriented toward different portions of an eye area of the user. In other words, a first sensor may be oriented toward a first portion of an eye area of the user, e.g. the eye itself, and a second sensor may be oriented toward a second portion of the same eye area, e.g. the eyelid. The sensors and the light source are preferably positioned around the eye area. In other words, the sensors and the light source may be positioned above and below the eye area. In this way, the line of vision of the user is clear so that the user is less disturbed by the sensing cells 21.

The sensors and/or light source are preferably configured to emit and receive, respectively, nonvisible light signals not to disturb the user. In doing so, the measurement is more accurate and better reflects the behavior of the user. More preferably, the sensors and light source are configured to emit and receive, respectively, infrared light signals. An infrared sensing cell 21 is merely a distance sensor which is used to measure a characteristic of the user's eye area. This infrared reflection measurement is very fast (from 1 to 100 khz) and allows the detection of high motion movements like a movement of the eye, a variation of the pupillary diameter or an eyelid blink.

Figures 5, 6:
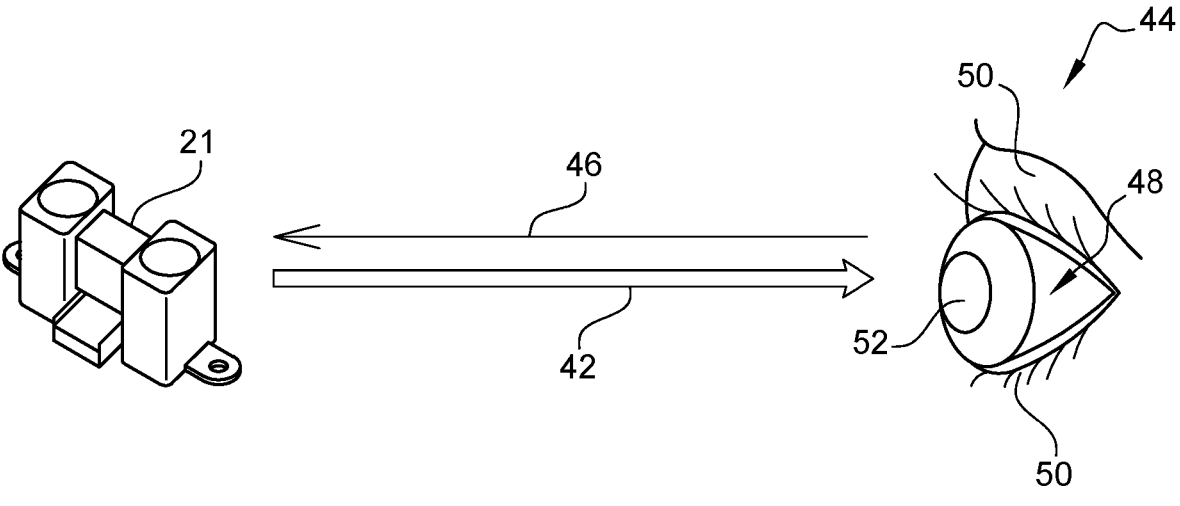
FIG. 5 schematically shows a first infrared signal emitted from an infrared sensor toward the eye area of a user and a second infrared signal reflected by the eye area toward the infrared sensor.
FIG. 6 schematically shows a scale to quantify the level of discomfort of a user when subjected to a light stimulation.

As shown on FIG. 5, the light source transmits a first signal 42 toward said at least one eye area 44 and the sensor receives a second signal 46 corresponding to the first signal 42 reflected by said at least one eye area 44. It thus possible to calculate how much infrared rays of the first signal 42 are reflected by the object in front of the infrared cell 21. Different materials have different reflectivity so that it is possible to know that a different material is positioned in front of the infrared cell 21 by comparing the difference between the first 42 and the second 46 signals. As an example, the reflectivity of the eye 48 and the reflectivity of the eyelids 50 are different. A variation between two consecutive second signals 46 thus occurs when the infrared rays are reflected first by the eye 48 and then by an eyelid 50. The same variation occurs when the infrared rays are reflected by different materials. It is thus possible to determine a variation of the position of one eyelid 50 or the pupil 52 as well as a variation of the size of the pupil 52. The variation of these characteristics may be representative of a visual discomfort of the user, for example. It is therefore possible to correlate a variation of at least one of these characteristics with a change in the visual comfort of the user.

The device 10 may also comprise at least one stimuli source for stimulating at least one eye of the user. Said stimuli source aims at inducing a variation of at one least one characteristic of the eye area. As an example, emitting light towards the eye of the wearer at a high luminance may induce a closure of the eyelid, contraction of muscles and a contraction of the pupil. This stimuli source is particularly useful when the behavior which is determined is a change in the visual comfort or performance, as glare.

According to one embodiment, which may be considered alone or in combination, the light stimuli source may be the light source. Like that, the light stimuli source is used both to stimulate and to be acquired by the sensing unit after to be reflected on the eye area. Said stimuli source is preferably lodged in the cavity 16 formed by the casing 31 of the device 10. Said stimuli source may be combined with a diffuser 12 disposed within the cavity 16 in front of the user's eyes to provide a diffused light. In this case, the stimuli source emits light toward the diffuser 12. Alternatively or in combination, the stimuli source may be positioned to emit light directly toward one or both eyes of the user. Hence, the device 10 may be configured to expose the user to either a homogeneous or punctual light, or both simultaneously.

Stimuli source preferably comprises at least one light-emitting diode (LED) able to have variable light spectrum as RGB LEDs (Red-Green-Blue light emitting diodes) or RGB-W LEDs ((Red-Green-Blue-White light emitting diodes). Alternatively, said stimuli source may be configured to provide a predetermined single white light spectrum or, alternatively, a spectrum having all visible radiations with substantially the same intensity, in contrast with a spectrum having peaks. Said at least one stimuli source is preferably controlled with a constant current to obtain a constant light flux coming out said at least one stimuli source. Providing the user with a constant light flux allows to reduce or avoid biological effects disturbances compared to stimuli sources controlled with Pulse Width Modulation (PWM).

The light signals received by the sensor may be a light source comprised in the sensing cell, may be a light source not comprised in the sensing cell, may be the light stimuli source or may be external light such as ambient light or light of a room.

According to an embodiment of the device, which can be considered alone or in combination, the at least one sensor is being associated to at least one light source.

According to an embodiment of the device, which can be considered alone or in combination, the sensing unit comprises at least one light source. By "associated", we mean that the sensor and the light source are synchronized in frequency/temporally and/or that the light source is oriented towards the eye area.

This embodiment presents the advantage to reduce the ratio signal under noise.

When the acquired signal concerns the position of at least one eyelid, the sensing unit 20 is thus able to acquire a signal representative of a closing/opening state of the eye. Furthermore, the position of one or two eyelids allows to determine a frequency of blink, an amplitude of blink, a duration of blink and different patterns of blink.

When the acquired signal concerns the position of the pupil, the sensing unit 20 is able to acquire a signal representative of the position of the eye itself. Then, when the acquired signal concerns the size of the pupil, the sensing unit 20 is able to acquire a signal representative of the dilatation/retraction level of the pupil.

A variation of one or more of the position of at least one eyelid, the position of the pupil and the size of the pupil can be representative of different behaviors. It is then possible to correlate the light conditions experienced at the time the variation occurs to a behavior of the user.

The device 10 further comprises a controller connected to the sensing unit 20 to receive the acquired signals from the sensing unit 20. The controller may be fully or partly embedded within the casing 31. The controller may be partly disposed within an external terminal. The controller may be remote.

The controller is configured to provide a machine learning algorithm. The device 10 is therefore a machine learning-based equipment for determining a behavior of a user.

A machine learning algorithm takes as input a training set of observed data points to "learn" an equation, a set of rules, or some other data structure. This learned structure or statistical model may then be used to make generalizations about the training set or predictions about new data. As used herein, "statistical model" refers to any learned and/or statistical data structure that establishes or predicts a relationship between two or more data parameters (e.g., inputs and outputs). Although the invention is described below with reference to neural networks, other types of statistical models may be employed in accordance with the present invention.

For example, each data point of the training data set may include a set of values that correlate with, or predict, another value in the data point. In the present invention, the machine learning algorithm is configured to correlate objective data related to the acquired target signals provided to the machine learning algorithm as inputs to a behavior of the user.

Said machine learning algorithm of the controller may be based either on a Long short-term memory (LSTM) technique or a convolutive neural network (CNN).

LSTM technique is part of recurrent neural networks (RNNs). Classical RNNs techniques comprise a network of neural nodes organized in successive layers. Each node (neuron) in a given layer is connected one-way to each of the nodes in the next layer. This structure allows previous moments to be taken into account in the neural network, since a first layer for a former moment t–1 is connected to second layer for a moment t. This second layer is also connected to a third layer for a subsequent moment t+1, and so on with a plurality of layers. Each signal provided as an input is therefore processed in a temporal way, taking into account the signals provided at former moments.

CNN techniques use the signals as images, not in a temporal way. The plurality of acquired signals are processed at once with all the data acquired for a test duration.

The machine learning algorithm may comprise a guiding model defining determination rules configured to guide the prediction of the machine learning algorithm. These rules may comprise sub-correlations between the target data and various behaviors. For example, this guiding model may provide that a given variation of a characteristic has to be correlated to a certain behavior. In another example, the guiding model may provide that a predetermined combination of variation of characteristics implies a certain behavior or a list of potential behaviors. This guiding model allows to ease the correlation made by the machine learning and therefore both reduces the time taken by the correlation and improves its accuracy.

The controller may use a machine learning algorithm which is already trained, i.e. the neural network of the machine learning algorithm already comprises an equation or a set of rules configured to provide a correlation between variations physical characteristics of the eye area of a user to a behavior of said user. Alternatively, the controller is configured to train the machine algorithm to determine to correlation.

Training of the machine learning algorithm is preferably performed by providing the algorithm with a plurality of initial data related to a set of initial users. By "initial users" we mean users which participate to the learning of the machine learning algorithm. In other words, initial users provide objective and/or subjective data allowing the machine learning algorithm to correlate physical variation of the eye area to different behaviors. To the contrary, a "target user" refers to a user for which a behavior determination is performed on the basis of the machine learning algorithm, i.e. for which a prediction of his behavior may be performed.

Said initial data comprise a plurality of acquired learning signals representative of a variation of at least one characteristic of at least one eye area for each initial user of the set. Said initial data may comprise subjective and/or objective data. Said subjective data may comprise the perception of the initial user to a behavior caused by said variation of at least one characteristic of at least one eye area.

This training is repeated many times to make the algorithm more accurate. As an example, training the algorithm may imply at least one hundred initial users.

The process for determining a behavior of a target user is then performed by acquiring a plurality of target signals representative of a variation of at least one characteristic of at least one eye area of a target user. A target signal refers to a signal representative of the eye area of the target user. In a similar way, an initial signal refers to a signal representative of the eye area of an initial user.

Said target data may comprise subjective and/or objective data.

Objective data refer to any value relative to the measurement of at least one parameter characteristic of a state of the structure and ocular functions or of the related structures via an optical and/or photometric measurement. The choice of such a representative quantity makes it possible to quantify, via a physical measurement, the capacities and performance of one or more ocular or related structures in relation with the glare processes.

Subjective data refer to verbal responses expressed by the user or any action of the user representative of its discomfort or visual perception. Subjective data may comprise the perception of the target user to a behavior, notably a behavior caused by said variation of at least one characteristic of at least one eye area. This subjective data may be obtained with an action of the target user onto the device 10 via a dedicated interface. Subjective data may also be obtained with information provided by the target user on his feelings. This subjective data may improve the accuracy of the behavior determination. Objective data refer to target signals representative of a variation of at least one characteristic of at least one eye area of a target user.

The machine learning algorithm of the controller is then provided with said plurality of target signals and determine a behavior of said target user as an output of the machine learning algorithm.

Figure 7:
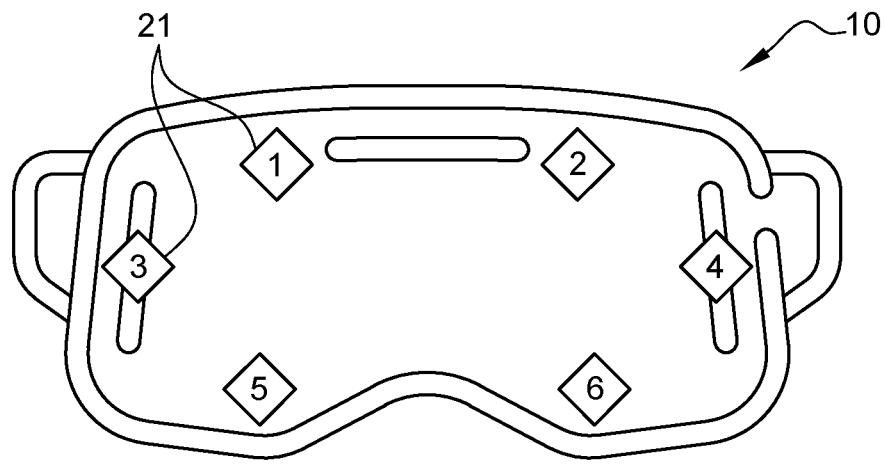
FIG. 7 schematically shows a front view of the binocular optoelectronic device of FIG. 1 wherein sensing cells are numbered.

An example of behavior determination is described below in reference to FIGS. 6 to 8. In this example, the behavior which is determined is glare. For this determination, a light sensitivity test is performed using the stimuli source to induce glare of the target user.

In use, the device 10 is positioned on the target user's head so that the sensing unit 20 faces at least one eye area of the target user. Different levels of light intensity are provided to the eyes of the target user. At the beginning of the test, the light intensity is very low, and is progressively increased to measure the sensitivity threshold of the patient.

A preferred sequence of light stimulation is described below.

A continuous light emission may be provided to induce an illuminance from a minimum to a maximum values increasing the illuminance by stages, e.g. from 25 Lux to 10211 Lux. For example, the light emission may start with an illuminance of 25 Lux for 5 seconds to adapt the eye to the light condition and cancel all previous light exposure before the measurement and then continue with an increase of the illuminance of 20% each second to the maximum illuminance. In a more general way, the light may be emitted to induce an illuminance varying from 25 Lux to 10000 Lux. This continuous light emission may be performed with warm light. Another continuous light emission may be performed with cold light.

Then, a flashing light emission is performed to induce an illuminance from a minimum value to a maximum value increasing the illuminance by stages, e.g. from 25 Lux to 8509 Lux. The illuminance of the flashing light emission is preferably increased by at least 30%, preferably by 40%, most preferably by at least 44%. Before and between each flashlight emission, the user is subjected to a light emission lower than the minimum value of illuminance of the flashing light emission, e.g. 10 Lux. The time of each flashing light emission is preferably 0.5 s and the time between each flashing light emission is preferably 2 s.

During this light stimulation, the sensing unit 20 acquires target signals representative of a variation of characteristics of the eye areas of the target user. Target signals may be continuously or intermittently acquired and transmitted to controller.

Target data are determined depending on these target signals. Said target data are then provided to the machine learning algorithm of the controller to determine potential glare of the target user. Particularly, the controller when the target user experience glare to be able to determine the light conditions which have cause glare. It is then possible to determine the light sensitivity of the target user with an automated process which do not necessarily involve subjective data from the target user.

In reference to FIG. 6, subjective data related to the target user may be obtained. The target user may be asked to press on a switch onto the device 10 to indicate his perception of the light stimulation. For example, the target user may press the switch once when the discomfort caused by light is "just perceptible" (see FIG. 6) and a second time when the discomfort is "really disturbing". The light stimulation is preferably turned-off after when the target user presses the switch for the second time.

Target signals recorded during a light sensitivity test are complex. About 200 000 data are acquired for each sensing cell 21 every second. An example of target signals acquired by the sensing cells 21 is shown on FIG. 8. Each sensing cell 21 is numbered from 1 to 6 as shown on FIG. 7.

Figure 8:
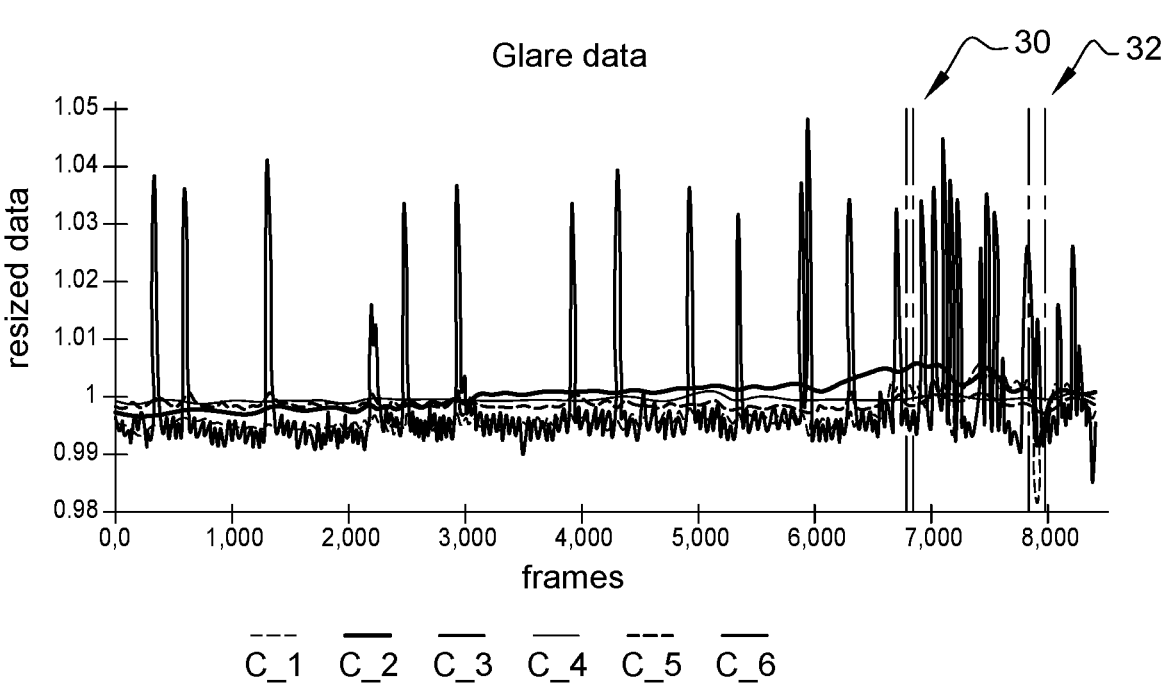
FIG. 8 is a graph showing data representative of signals acquired by sensing cells numbered in FIG. 7, with regard to a frame axis.

In reference to FIG. 8, about 40 seconds of data are shown. Indeed, sensing cells 21 acquire data at about 200 Hz so 8500 frames correspond to a measurement of about 40 seconds. Intensity of light rises up from the frame 0 to the frame 8000. A first reference 30 correspond to the moment when the target user has pressed the switch for the first time and a second reference 32 correspond to the moment when the target user has pressed the switch for the second time. The same kind of data is used to train the machine learning algorithm.

Depending on the results, target users are divided in a plurality of glare classes. These glare classes allow to classify users with respect to light sensitivity. Hence, these glare classes may for example be used for determining a filter for the target user, particularly a filter for a transparent support able to improve or to maintain the visual comfort and/or visual performance of said target user.

Classifying the target user among the glare classes may be performed by following either an indirect or a direct classification.

In the indirect classification, the machine learning algorithm is trained to detect when an initial user presses the switch. The algorithm then determines the glare class by reducing the time interval between the predicted click on the switch and the real click. In this way, the algorithm provides as an output the number of frames at which the algorithm predicts that the initial user would press the switch. With this frame, the controller is able to determine the illuminance of the light stimulation at the predicted time and then classify the target user accordingly.

In the direct classification, the algorithm is trained to directly determine the glare class of the target user.

A first classification may be considered. People may be divided in three parts: people which are very sensitive, people which are sensitive and people which are not sensitive. People in the first part generally have a light sensitivity threshold below 1000 lux and correspond to about 25% of the whole population. Then, people in the second part generally have a light sensitivity threshold between 1000 and 5000 lux and correspond to about 50% of the whole population. Finally, people in the third part generally have a light sensitivity threshold above 5000 lux and correspond to about 25% of the whole population Then, a second classification have been determined with a first trial involving 500 initial users. According to this second classification, people may be divided in four classes: a first class with a light sensitivity threshold below 600 lux (about 25% of the whole panel), a second class with a light sensitivity threshold between 600 and 2000 lux (about 25% of the whole panel), a third class with a light sensitivity threshold between 2000 and 4000 lux (about 25% of the whole panel) and a fourth class with a light sensitivity threshold above 4000 lux (about 25% of the whole panel).

Then, a second trial involving 200 initial user has been conducted to identify for each initial user of the second trial the relevant glare class according to the first and second classifications. Results of this second trial are shown in the table below.

| Test set | Accuracy of the first classification (3 classes) | Accuracy of the second classification (4 classes) |
|---|---|---|
| Random | 36% | 28% |
| Mean | 42% | 28% |
| Dominant class | 42% | 34% |
| Recurrent neural network | 58% | 58% |
| Fusion layer | 71% | 75% |
| Convolutive network | 71% | 46% |

Baselines are given by the three first lines referring to the "random", "mean" and "dominant class". These percentages indicate reference values on the accuracy of the glare classes for the initial users. These baselines correspond to the prediction of a random classification or a classification of the mean class, which are not obtained using a machine learning algorithm.

The values obtained with the recurrent neural network and fusion layer techniques belong to the indirect classification. The values obtained with the convolutive network technique belong to the direct classification.

The values obtained with the machine learning algorithm, using recurrent neural network, fusion layer and convolutive network techniques, are compared to the baselines. We can see that the results obtained with the machine learning algorithm are more accurate than the baselines. Particularly, the fusion layer technique allowed to obtain the more accurate results.

The method according to the invention and performed by the controller of the device 10 is computer-implemented. Namely, a computer program product comprises one or more sequences of instructions that are accessible to a processor and that, when executed by the processor, cause the processor to carry out steps of the method for determining the spectral transmittance of an ocular media of at least one eye of said user as well as determining at least one filter as described above.

The sequence(s) of instructions may be stored in one or several computer-readable storage medium/media, including a predetermined location in a cloud.

Although representative methods and devices have been described in detail herein, those skilled in the art will recognize that various substitutions and modifications may be made without departing from the scope of what is described and defined by the appended claims.

The invention claimed is:

1. A device for determining a behavior of a target user, comprising:
    a sensing unit configured to face at least one eye area of a target user, the sensing unit being configured to acquire a plurality of target signals representative of a variation of at least one characteristic of said at least one eye area of said target user,
        the sensing unit comprising at least one sensor, the at least one sensor being a non-imaging sensor, and
        the at least one sensor being oriented towards said at least one eye area;
    a light stimuli source configured to stimulate at least one eye, said behavior being a change in visual comfort of the target user, said variation of said at least one characteristic being caused by a light stimulus provided to said at least one eye area, and said change in the visual comfort of the target user being glare; and
    a controller configured to:
        provide a machine learning algorithm,
        stimulate at least one eye with said light stimuli source,
        provide a plurality of objective target data related to the acquired target signals as an input to said machine learning algorithm,
        determine a behavior of said target user as an output of the machine learning algorithm, and
        determine at least one filter for a transparent support to improve or to maintain the visual comfort and/or visual performance of said target user based on said behavior.

2. The device according to claim 1, wherein the at least one sensor is placed around said at least one eye area.

3. The device according to claim 1, wherein the at least one sensor is associated to at least one light source.

4. A computer-implemented method for determining a behavior of a target user, the method comprising:

providing a machine learning algorithm;

stimulating at least one eye with a light stimuli source;

acquiring a plurality of target signals representative of a variation of at least one characteristic of at least one eye area of a target user by using a sensing unit facing said at least one eye area of a target user, the sensing unit comprising at least one sensor, the at least one sensor being a non-imaging sensor, said behavior being a change in visual comfort of the target user, said variation of said at least one characteristic being caused by a light stimulus provided to said at least one eye area, and said change in the visual comfort of the target user being glare;

providing a plurality of objective target data related to the acquired target signals as an input to said machine learning algorithm;

determining a behavior of said target user as an output of the machine learning algorithm; and determining at least one filter for a transparent support to improve or to maintain the visual comfort and/or visual performance of said target user based on said behavior.

5. The computer-implemented method according to claim 4, wherein said machine learning algorithm is based on a plurality of initial data related to a set of initial users, said initial data comprising a plurality of acquired learning signals representative of a variation of at least one characteristic of at least one eye area for each initial user of the set.

6. The computer-implemented method according to claim 5, wherein said plurality of initial data related to a set of initial users comprises subjective and objective data, said subjective data comprising perception of the initial users of the set to a behavior caused by said variation of at least one characteristic of at least one eye area for each initial user of the set.

7. The computer-implemented method according to claim 5, further comprising:

providing to the machine learning algorithm said plurality of initial data related to a set of initial users; and training said machine learning algorithm with regard to said plurality of initial data.

8. The computer-implemented method according to claim 4, further comprising:

determining subjective data related to said target user, said subjective data comprising perception of the target user to said behavior; and providing said subjective data related to said target user as an input of said machine learning algorithm.

9. The computer-implemented method according to claim 4, wherein said behavior is a change in visual comfort of the target user, said variation of said at least one characteristic being caused by a light stimulus provided to said at least one eye area.

10. The computer-implemented method according to claim 9, further comprising determining a plurality of glare classes to classify initial users with respect to light sensitivity, said determining a behavior comprising determining a glare class among the plurality of glare classes corresponding to the behavior of said target user.

11. The computer-implemented method according to claim 4, wherein said behavior is a movement of at least one eye of the target user or a dimension of at least one pupil of the target user.

12. The method according to claim 4, wherein said at least one characteristic comprising at least one among a position of at least one eyelid, a position of a pupil, a size of the pupil and a muscle contraction in said at least one eye area.

* * * * *